(12) United States Patent
Covely

(10) Patent No.: US 10,444,122 B2
(45) Date of Patent: Oct. 15, 2019

(54) SOIL SAMPLE TRACKING SYSTEM AND METHOD

(71) Applicant: Agri-Labs Holdings LLC, Auburn, IN (US)

(72) Inventor: Tony Wayne Covely, Corruna, IN (US)

(*) Notice: Subject to any disclaimer, the term of this patent is extended or adjusted under 35 U.S.C. 154(b) by 1024 days.

(21) Appl. No.: 13/633,991

(22) Filed: Oct. 3, 2012

(65) Prior Publication Data

US 2014/0095074 A1 Apr. 3, 2014
US 2015/0153253 A9 Jun. 4, 2015

Related U.S. Application Data

(63) Continuation of application No. 12/752,269, filed on Apr. 1, 2010, now Pat. No. 8,286,857.

(51) Int. Cl.
| | | |
|---|---|---|
| *G01N 1/08* | (2006.01) | |
| *E02D 1/04* | (2006.01) | |
| *G01N 33/24* | (2006.01) | |
| *G01N 1/02* | (2006.01) | |

(52) U.S. Cl.
CPC ............... *G01N 1/08* (2013.01); *E02D 1/04* (2013.01); *G01N 33/24* (2013.01); *G01N 2001/021* (2013.01); *G01N 2033/245* (2013.01)

(58) Field of Classification Search
CPC ....................................................... G01N 1/08
See application file for complete search history.

(56) References Cited

U.S. PATENT DOCUMENTS

| | | | |
|---|---|---|---|
| 5,591,974 A † | 1/1997 | Troyer | |
| 5,991,667 A | 11/1999 | Hale et al. | |
| 5,991,687 A † | 11/1999 | Hale | |
| 6,016,713 A * | 1/2000 | Hale | A01B 79/005 |
| | | | 73/864.45 |
| 6,044,324 A | 3/2000 | Boerhave et al. | |
| 6,947,866 B2 | 9/2005 | Staab | |
| 6,963,881 B2 | 11/2005 | Pickett et al. | |
| 7,113,922 B2 † | 9/2006 | Fowler | |
| 7,552,654 B2 | 6/2009 | Burton | |

(Continued)

FOREIGN PATENT DOCUMENTS

| | | |
|---|---|---|
| CA | 2526883 | 6/2007 |
| CA | 2529883 † | 6/2007 |

OTHER PUBLICATIONS

AgFleet Helpdesk, How to Mark Target Samples, 2007.
(Continued)

*Primary Examiner* — Manuel A Rivera Vargas
(74) *Attorney, Agent, or Firm* — Indiano Law Group LLC

(57) ABSTRACT

A system and method for performing soil analysis is disclosed. The method comprises generating a plurality of soil sample containers each having a unique identifier associated therewith. Pulling at least one soil sample from a field and placing the at least one soil sample in a respective one of the plurality of soil sample containers. Scanning the unique identifier associated with the soil sample container containing the at least one soil sample with a remote terminal. Obtaining a geographic coordinate reading associated with a location in the field from where the soil sample is obtained and associating the soil sample with the unique identifier and the geographic coordinate reading.

28 Claims, 6 Drawing Sheets

(56) References Cited

U.S. PATENT DOCUMENTS

| | | | |
|---|---|---|---|
| 2002/0035431 A1* | 3/2002 | Ell | A01B 79/005 |
| | | | 702/5 |
| 2002/0091593 A1 | 7/2002 | Fowler | |
| 2005/0187733 A1* | 8/2005 | Staab | G01N 1/02 |
| | | | 702/150 |
| 2005/0197175 A1 | 9/2005 | Anderson | |
| 2005/0197177 A1† | 9/2005 | Anderson | |
| 2006/0106539 A1* | 5/2006 | Choate | G06Q 10/10 |
| | | | 702/2 |
| 2007/0075141 A1 | 4/2007 | Veitch et al. | |
| 2008/0085506 A1 | 4/2008 | Bjorndal et al. | |
| 2008/0229805 A1 | 9/2008 | Barket et al. | |
| 2009/0057422 A1 | 3/2009 | Dugas et al. | |
| 2009/0198541 A1 | 8/2009 | Dolan et al. | |

OTHER PUBLICATIONS

AgFleet Overview 2008, Product Outputs, 2008.
AgFleet, Field Sampler Product Outputs, 2008.
AgFleet, ZedX Innovations for Decision Making, 2007.
AgFLeet-Field Sampler, ZedX Inc, 2008.
AgGPS 160 Portable Computer, Support Note, Connecting Equipment to the AgGPS 160 Portable Computer, Nov. 2001.
AgGPS Field Manager Quick Reference Card, 2002.
David Hest, Online crop control—Web-based software allows easy access to crop data, farmindustriesnews.com, Aug. 2009.
Farm Site Website printout, May 25, 2007.
Farm Trac, Field record-keeping software article, Feb. 26, 2008.
Trimble Nomad Handheld Computer Datasheet, Nov. 2008.
Trimble Nomad, Information Management Solutions—Website Printout, 2009.
Trimble Press Release, Trimble Acquires Farm Works Software Assets to Explain its Precision Agriculture Solutions, Jul. 17, 2009.
Trimble Press Release, Trimble Expands EZ-Office Agriculture Software Capabilities for Field and Office, Nov. 20, 2009.
Trimble Press Release, Trimble Introduces New Nomad 800X Series Rugged Handhelds, Jan. 7, 2009.
Trimble press release, Trimble Introduces Nomad Rugged Handheld Computer with 806 MHz Processor VGA Display, Integrated GPS, Wireless and Optical Capabilities, Jul. 17, 2007.
Trimble Press Release, Trimble Nomad Rugged Handheld Computers with Digital Camera and Bar Code Scanner Now Available, Nov. 5, 2007.
Trimble, News Press Release, Trimble Continues to Add Value to Precision Farming, Feb. 11, 1999.
Trimble, Technical Notes, AgGPS 170 Field Computer, Rugged Field Computer for Precision Agriculture, 2002.
FarmLogic Overveiw, A Simple Farm Information Management System Has Arrived. Finally!, Sep. 22, 2008.
Hui Fang, Yong He, A Pocket PC based field information fast collection system, Received Aug. 30, 2004.
R. Scott Nusbaum-Farm Works Software, Site Mobile and Farm Works Software, Jun. 18, 1999.
R.D. Buick, Precision Agriculture: An Integration of Information Technologies With Farming, 1997.
TDS Nomad, Website Printout, Sep. 21, 2008.
Trimble AgGPS 170 Field Computer User Guide, Mar. 2001.
Trimble Agriculture Product Bulletin, EZ-View and EZ-Office Software: 2010 Software Editions Now Available, Nov. 19, 2009.
Trimble EZ-Office Mobile Software and the Trimble Nomad Handheld Computer, Nov. 2009.
Trimble Nomad Handheld Computer Getting Started Guide, Oct. 14, 2008.
Trimble News Press Release, Trimble Adds Portable Computer to AgGPS Product Line, May 18, 2001.
S.G. Borgelt, J.D. Harrison, K.A. Sudduth, S.J. Birrell. Evaluation of GPS for Application in Precision Agriculture. Applied Engineering in Agriculture. American Society of Agricultural Engineers. vol. 12(6), pp. 633-638.
George B. Frisvold. Data, Information, and Rural Environmental Policy: What Will the Next Ten Years Bring? Review of Agricultural Economics. Oxford University Press. vol. 22, No. 1 (Spring-Summer 2000), pp. 237-244.
Cecil H. Yancy, Jr. Data on tap. Mid-South Farmer. Jan. 2009, p. 1.
Farm Works Software. Barcode reader for soil samples with Site Mate. Search Discussion Boards, Nov. 2, 2009.
www.youtube.com/watch?v=MOhhCpalOta. Data hand held collection in the field. Uploaded Sep. 3, 2008.
Programmers Stack Exchange. http://programmers.stackexchange.com/questions/95589/boss-doesnt-believe-my-time-estimate-advice-backup. Dealing with bad/incomplete/unclear specifications? Sep. 25, 2009.
https://www.youtube.com/watch?v=MOhhCpalOtA Video for Trimble Nomad uploaded Sep. 3, 2008.†
http://programmers.stackexchange.com/questions/95589/boss-doesnt-believe-my-time-estimate-advice-backup Matt G. Website Forum Sep. 25, 2009.†
http://farmworks.com/forum/read.php?10,58037 Website forum publication Nov. 2, 2009.†
Cecil H. Yancy, Jr., Data on Tap, Mid-South Farmer, Jan. 2009.†

\* cited by examiner
† cited by third party

SOIL SAMPLE TRACKING SYSTEM AND METHOD

CROSS REFERENCE TO RELATED APPLICATION

The present application is a continuation application of and claims the benefit of U.S. application Ser. No. 12/752,269 filed on Apr. 1, 2010, and which issued as U.S. Pat. No. 8,286,857 on Oct. 16, 2012, which is hereby incorporated by reference in its entirety.

BACKGROUND

The present invention relates generally to soil sampling and more particularly, to a system and method of soil sampling to determine the nutrient level of soil in fields so that a variable-rate nutrient pattern or prescription can be generated for a particular field.

The agricultural industry uses soil samples to determine the nutrient level of soil in fields. Soil sampling and testing provides an estimate of the capacity of the soil to supply adequate nutrients to meet the needs of growing crops. In some instances, the test results are compared to standard response data associated with specific types of crops to estimate the need to supply additional nutrients for optimum crop production. The test results are then used as a basis for profitable and environmentally responsible fertilizer application.

Typically, about a teaspoonful of soil is actually used for laboratory analysis. That small amount represents the entire area for which the fertilizer recommendation is made for that particular area. Several soil samples are typically taken from a given field and represent an area of the field. The soil samples are often taken using different soil sampling pattern options. A grid pattern is usually the best way to ensure that the entire field is represented. In this form, a given field is divided up into various cells with each cell representing an area of the field. For illustrative purposes only, a sixty acre field could be divided up into thirty cells with each cell representing two acres of the field. A sample is taken from each cell to generate a representative nutrient map of the field.

Currently, most soil samplers use a computer to guide them to the correct location of the field from which samples are taken. The soil samplers use a probe to take the soil sample and the soil is then placed in a container which is sent to a lab for soil analysis. The soil samplers must have some way of identifying one container from another. One way to do this is to handwrite specific information on each container. For example, each container may have handwritten material placed on them identifying a client name, farm name, field name and a sample identification. This method is very time consuming and can be filled with errors at the lab by misreading the written information.

A second way is to print labels ahead of time in the office and take them out to the field when gathering samples. After each soil probe, the soil sampler applies a label to the container, thereby distinguishing it from other containers. This method is also problematic because of the tendency to put the wrong label on the container and it is also time consuming. When the soil sampler is done collecting the samples they are shipped off to the lab where the samples can be processed and fertilizer recommendations can be made. Both of the above-described techniques for container identification are very time consuming for lab technicians as well as the soil samplers. Receiving containers with either handwritten information or printed labels causes the lab technicians to have to re-enter this information into a computer at the lab. This is also another area in which mistakes are easily made thereby causing samples to fail to get matched up with the right information. Once the samples are processed or analyzed at the lab, the test results are sent to the customer who may then import that data into a software application for processing of application maps for fertilizer.

SUMMARY

One embodiment according to the present invention discloses a unique system for performing soil analysis of a field. Another embodiment according to the present invention discloses a unique system for performing a soil analysis of a field and generating a visual display of the test results. Other embodiments include unique apparatuses, systems, devices, hardware, software, methods, and combinations of these for performing soil analysis. Further embodiments, forms, objects, features, advantages, aspects, and benefits of the present invention shall become apparent from the following description and drawings.

DESCRIPTION OF THE ILLUSTRATED EMBODIMENTS

Figure 1:
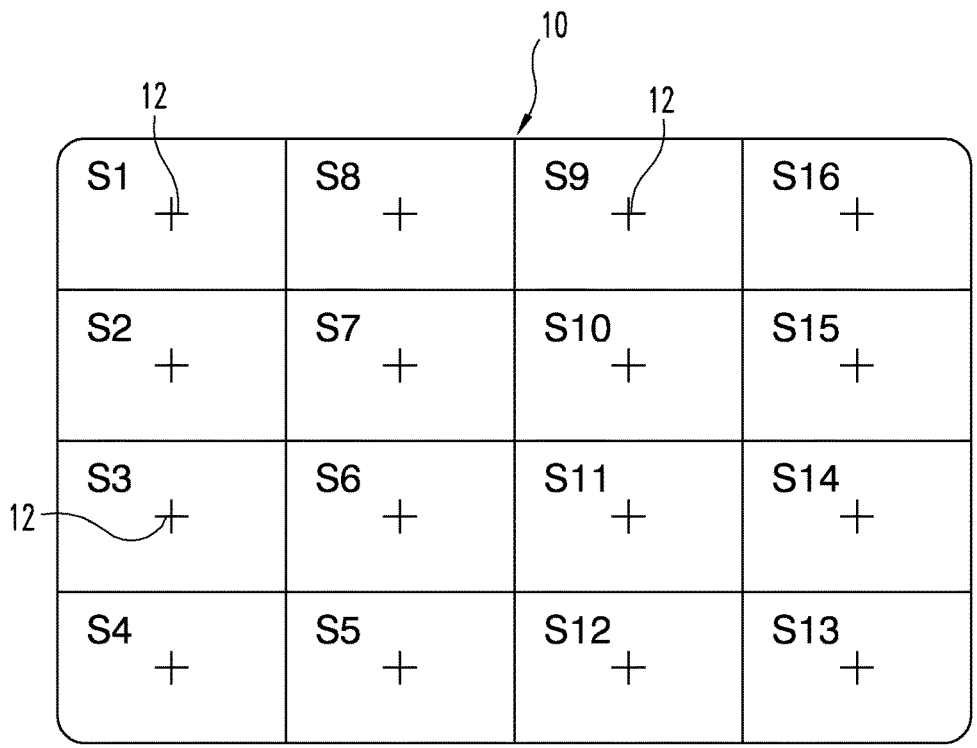
FIG. 1 illustrates a field that has been divided up into a plurality of sample cells.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Referring to FIG. 1, a field 10 is illustrated that has been divided up into a grid-like pattern that includes a plurality of sample cells S1-S16. For illustrative purposes only, the field 10 illustrated in FIG. 1 could be representative of a thirty-two (32) acre field that has been divided up into sixteen (16) sample cells S1-S16. As such, in this illustrative example, each sample cell S1-S16 represents approximately two (2) acres of land. Although the sample cells S1-S16 are illustrated as having a generally rectangular shape, it should be appreciated that the size and shape of the sample cells S1-S16 for a given field can vary depending on the size and shape of the field 10 and so on. In addition, the field 10 could be divided up into other patterns other than a grid-like pattern in other forms of the present invention.

As further illustrated in FIG. 1, in order to determine the nutrient level of the soil at any given location in the field 10, a plurality of core soil samples 12 must be taken from various locations in the field 10. In this representative form, a core soil sample 12 is taken from within each sample cell S1-S16. Although the core soil samples 12 are illustrated as being taken in a regular systematic grid-like pattern, it should be appreciated that the core soil samples 12 can be taken from the field 10 in other ways as well. For example, the core soil samples 12 could be taken in a staggered start pattern, a random pattern, a systematic unaligned grid pattern, and so forth.

Figure 2:
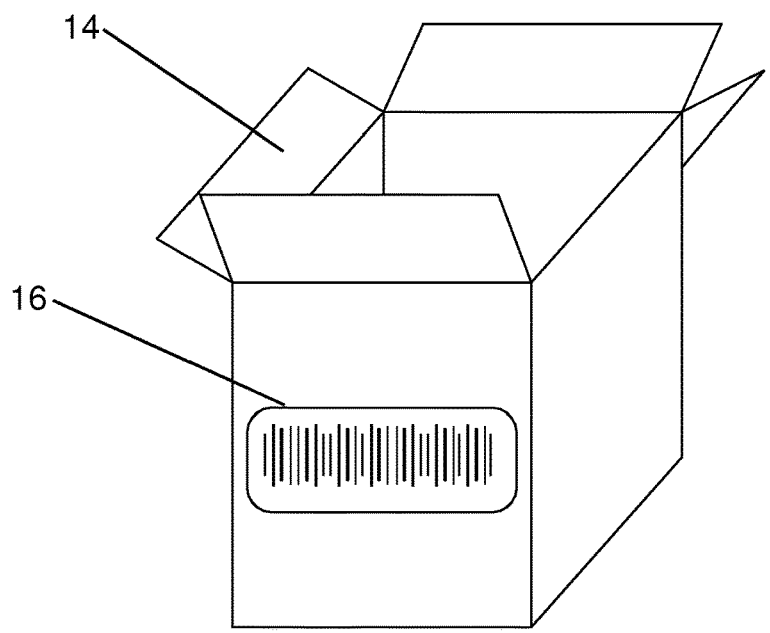
FIG. 2 illustrates a container having a unique machine readable identifier associated therewith.

Referring to FIG. 2, once the core soil samples 12 are taken from the desired location in the field 10, each individual core soil sample 12 is placed into a unique soil sample container 14. As will be discussed in greater detail below, each container 14 has a unique machine readable identifier 16 (e.g. —barcode) associated with it so that each container 14 can be readily identified. Although illustrated as a box in FIG. 2, it should be appreciated that the containers 14 can come in any form suitable for temporarily storing soil samples for laboratory testing such as, for example, bags, bottles, and so forth.

Figure 3:
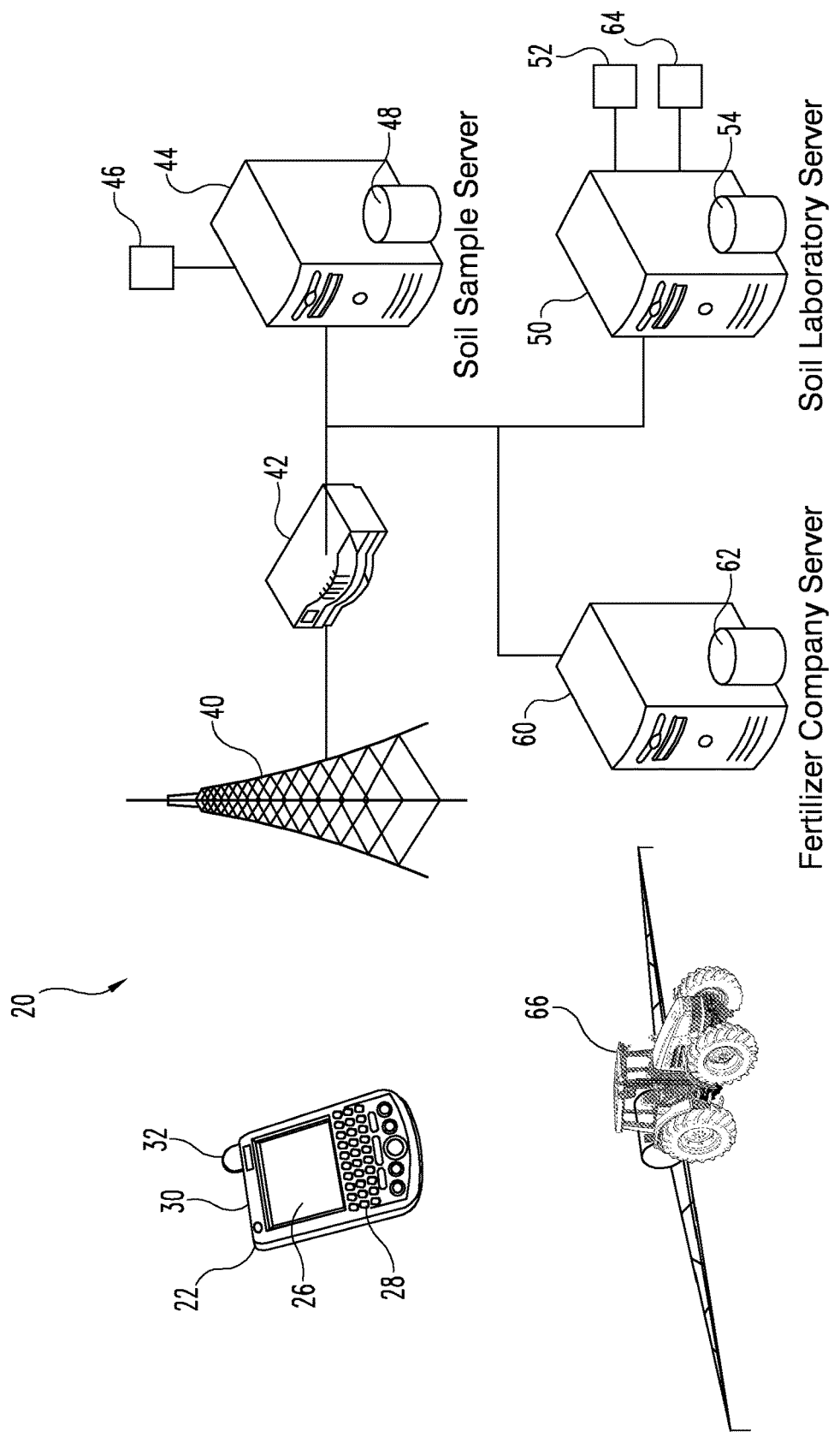
FIG. 3 illustrates a soil analysis system according to one aspect of the present invention.

Referring to FIG. 3, the present invention discloses a system 20 for acquiring soil samples from an agricultural field 10 for analysis and for providing a nutrient prescription for a particular field 10 for use by a fertilizer company or farm. As illustrated, in one form of the present invention the system 20 includes a handheld or remote wireless terminal 22 that is operable to be connected with a wireless communication network 24. Wireless terminal 22 includes a display 26, a keypad 28, a scanner 30, and a Global Positioning System (GPS) receiver 32. In other forms, the wireless terminal 22 includes a Differential Global Positioning System (DGPS) receiver 32. The GPS or DGPS unit 32 is operable to provide the wireless terminal 22 with accurate readings on the geographic location of the wireless terminal 22. In particular, in one form the wireless terminal 22 is capable of generating a longitude coordinate reading and a latitude coordinate reading that correspond to the geographic location in which a soil sample 12 is taken from the field 10.

The scanner 30 is configured and operational to scan the unique identifier 16 associated with the containers 14 as the soil samples 12 are taken from the field 10. In one form, as a respective soil sample 12 is taken at a location in the field 10, the soil sample 12 is placed in the container 14, the unique identifier 16 on the container 14 is scanned, and then the wireless terminal 22 automatically stores the geographic coordinates associated with the soil sample 12 and associates the soil sample 12 with the unique identifier 16 and the geographic coordinates. This allows the user of the wireless terminal 22 to associate each container 14, and thus each soil sample 12, with a specific geographic location in the field 10. The user is not required to individually label or use written records of any kind in order to store information about each soil sample 12 taken from the field 10.

In one form of the present invention, the system 20 includes a wireless transceiver 40 that is configured to transmit wireless data to the wireless terminal 22 and receive data being transmitted from the wireless terminal 22. The wireless transceiver 40 is connected with a router 42 that routes data to a soil sample server 44. In another form, the soil sample server 44 includes a connection member 46 (e.g. —docking station, USB cable, serial cable, parallel cable, and so forth) that allows the user to connect the wireless terminal 22 with the soil sample server 44 to upload data records. Once connected, the wireless terminal 22 is configured and operational to upload data to the soil sample server 44. As further illustrated, the soil sample server 44 includes a database 48 that is configured to store data. As set forth in greater detail below, this data preferentially includes a plurality of farm identifications, soil sample container identifier information (i.e. —identifiers 16), geographic coordinate information associated with a respective container 14, and soil analysis test results. In other forms, the wireless terminal 22 could communicate directly with a laboratory server 50, a laptop or computer owned by the sampler which could transmit the data to the soil sample server 44 or the laboratory server 50, and so forth.

The system 20 also includes a soil laboratory server 50 that is connected with the soil sample server 44. The soil laboratory server 50 is connected with one or more pieces of soil analysis equipment 52 that are configured to run various tests on the soil samples 12. The soil analysis equipment 52 may test the following attributes of each soil sample 12: the acidity or alkalinity level (pH levels), buffer pH levels (BpH), Cation Exchange Capacity (CEC) levels, potassium levels ($K^+$), sulfur levels ($S^+$), ammonium levels ($NH_4^+$), magnesium levels ($Mg^{++}$), calcium levels ($Ca^{++}$), zinc levels ($Zn^+$), manganese levels ($Mn^{++}$), iron levels ($Fe^{++}$), copper levels ($Cu^+$), hydrogen levels ($H^+$), and so forth. While hydrogen is not a nutrient, it affects the degree of acidity (pH) of the soil, so it is also important. For the purpose of the present invention, it should be appreciated that almost any type of test may be ran on the soil samples 12 to obtain a reading of an attribute of interest. As a result, a plurality of soil sample test results are generated that are stored in a soil analysis database 52 associated with the soil laboratory server 50. In one form, the soil sample test results are transmitted to the soil sample server 48 and in yet another form, the soil sample test results are transmitted to a fertilizer company server 60 connected with the soil laboratory server 50 and the soil sample server 44. The fertilizer company server 60 stores the soil sample test results in a database 62 and the soil sample server 44 also stores the test results in database 48. The fertilizer company server 60 could also be a consulting firm server or a server that is maintained by a farmer or customer.

Figure 4:
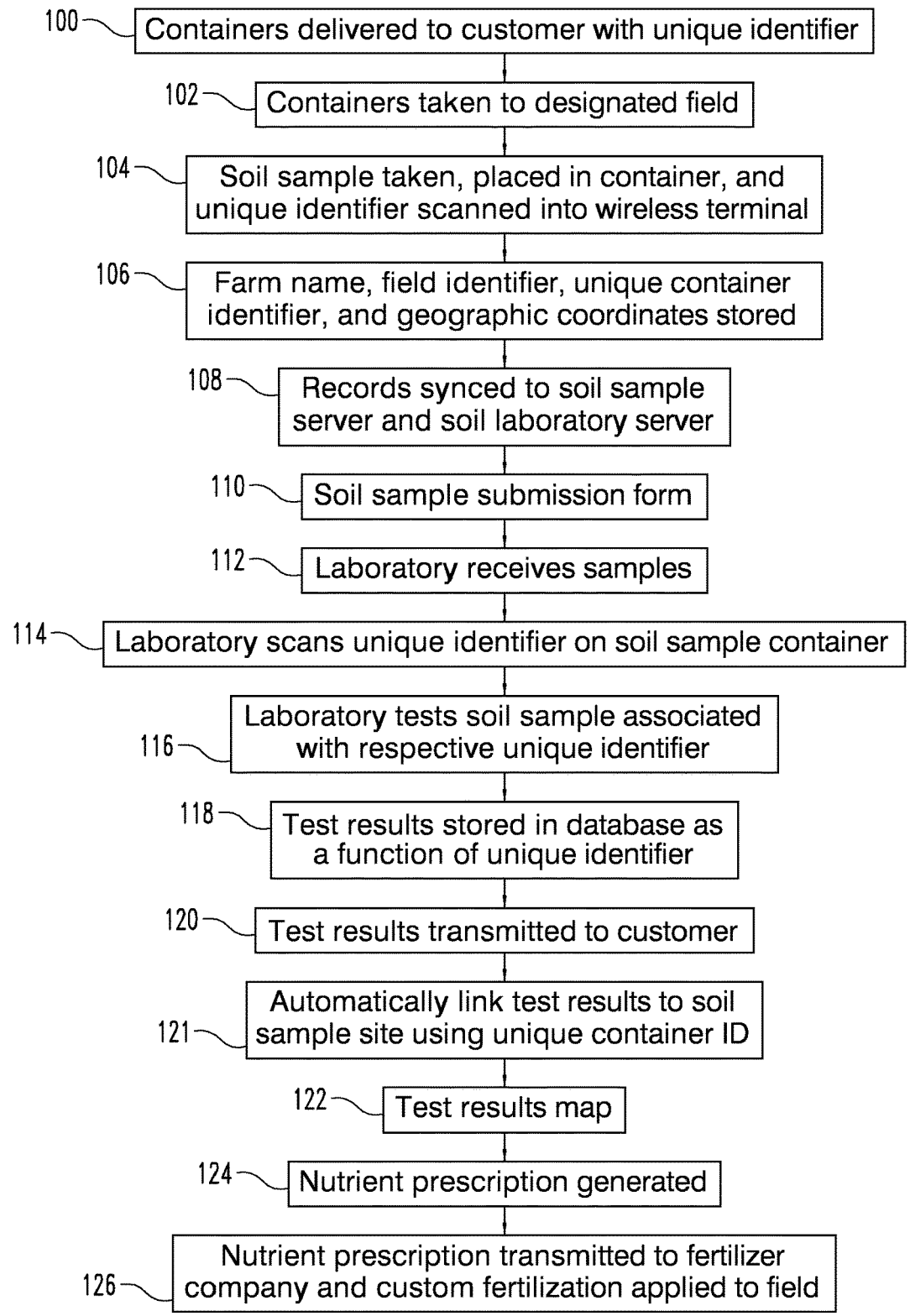
FIG. 4 is a flow chart illustrating certain steps performed in the present system.

Referring to FIG. 4, a more detailed explanation of system 20 will be discussed. At step 100, a plurality of containers 14 are delivered to a sample taker or customer. As set forth above, a unique machine readable identifier 16 is associated with each respective container 14. At step 102, the sample taker takes the containers 14 to a designated field 10 of a client of the sample taker. At step 104, the sample taker takes a soil sample 12 from the field 10 and places it in the container 14. The sample taker then scans the unique identifier 16 on the container 14 using the scanner 30 on the wireless or remote terminal 22.

Figure 5:
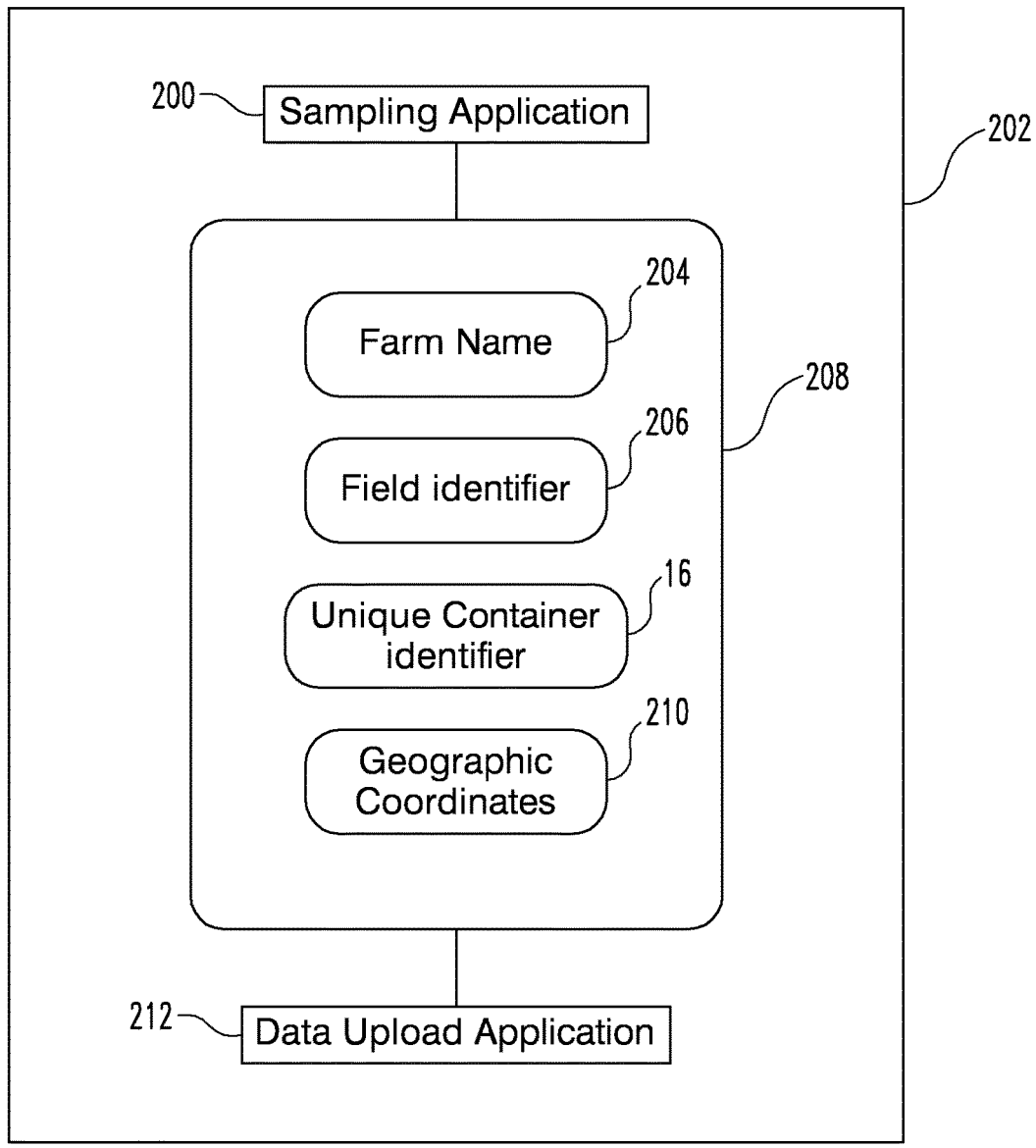
FIG. 5 illustrates certain software applications and databases contained on a wireless terminal associated with the system.

Referring to FIG. 5, the wireless terminal 22 includes a sampling application 200 that is stored in a memory device 202 of the wireless terminal 22. In other forms, the sampling application 200 could wirelessly be provided to the wireless terminal 22 from the soil sample server 44 in the form of a browser based web application or custom application. The sampling application 200 is configured to allow the sample taker to enter a farm/client name 204 and a field identifier 206. The field identifier 206 can be provided by the field owner (e.g. —Smith Field 1) or could be in the form of an address. In the case of an ongoing client, the sampling application 200 is configured to allow the sample taker to pull up a client name 204 and field identifier 206 already stored in a database 208 on the wireless terminal or on database 48 of the soil sample server 44.

The sampling application 200 is also configured to allow the sample taker to scan the unique identifier 16 on the container 14 using the scanner 30 of the wireless terminal 22 as the soil samples 12 are taken from the field 10. As previously set forth, the soil samples 12 can be take from the field 10 from various sample cells S1-S16. Once the wireless terminal 22 is used to scan the unique identifier 16 on the container 14, a record 254 (see FIG. 6) is automatically generated by the soil sampling application 200 that is stored in the database 208 of the wireless terminal 22 or transmitted to the soil sample server 44 for storage in database 48, which is represented at step 106 in FIG. 4. In one form, the record 254 includes the farm/client name 204, the field identifier 206, the unique container identifier 16, and a geographic coordinate reading 210. See FIG. 5. As such, each record 254 is associated with a respective container 14 via the unique identifier 16 on each of the containers 14.

Referring collectively to FIGS. 4 and 5, at some point in time, after all of the soil samples 12 have been taken from cells S1-S16 in the field 10 in one form of the present invention, the records 254 generated by the sample taker using the wireless terminal 22 in the field 10 are uploaded or synced with the soil sample server 44, which is represented at step 108. In other forms, the records 254 created by the sampling application 200 can automatically be transmitted to the soil sampling server 44 and stored in database 48 as the records 254 are generated by the soil sampling application 200. In yet another form, the wireless terminal 200 can be connected with the soil sampling server 44 with the connection member 46 and then the records 254 can be uploaded to the soil sampling server 44. The wireless terminal 22 includes a data upload application 212 that is configured to control how records 254 are transmitted to the soil sample server 44. All records 254 generated are stored in the database 48 associated with the soil sample server 44. In the illustrated example, sixteen (16) records would be generated and transmitted to the soil sampling server 44 for the field 10. This represents one record 254 for each sample cell S1-S16.

Referring to FIG. 4, at step 108 the records 254 could also have been synced or uploaded to the soil laboratory server 50. In some forms, the operator of the soil sample server 44 may not actually perform the soil analysis. As such, the records 254 generated by the soil sampling application 200 will need to be provided to the lab actually performing the soil analysis. In other forms, the owner of the soil sampling server 44 may actually perform the soil analysis, thereby eliminating the need for providing the records to 254 the soil laboratory server 50. In this form, the soil analysis equipment 52 would be connected or associated with soil sample server 44.

The sample taker may generate a soil sample submission form 110. The soil sample submission form 110 can be generated automatically by the soil sampling application 200 after the soil samples 12 have all been collected or manually generated by the soil sampler. The soil sample submission form 110 is used for shipment or transport of the soil samples 12 to the laboratory for analysis. At step 112, the laboratory responsible for testing the soil samples 12 (either the owner of soil sample server 44 or a third party laboratory responsible for soil laboratory server 50) receives the soil samples 12. For the sake of brevity, during the remainder of this detailed description it will be assumed that a third party laboratory is responsible for testing the soil samples. However, it should be appreciated that the soil analysis may be performed at the same location to which the records 254 are originally reported (i.e. —the soil sample server 44).

Figure 6:
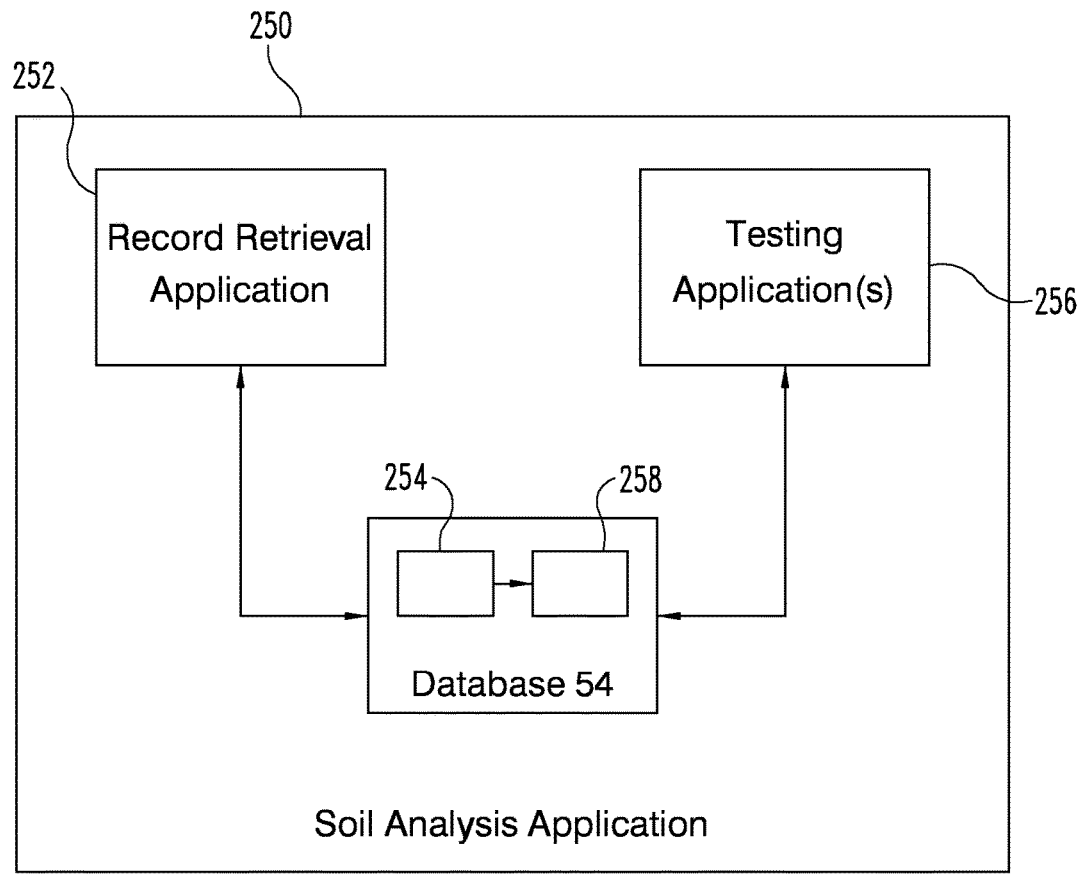
FIG. 6 illustrates a representative soil analysis application.

Referring to FIGS. 3, 4, and 6, once the soil samples 12 reach the lab, a scanner 64 connected or associated with the soil laboratory server 50 is used to scan the unique identifier 16 of each container 14 as each soil sample is analyzed, which is represented at step 114. The soil laboratory server 50 includes a soil analysis application 250 that is configured and operable to generate test results that are associated with the soil samples 12. The soil analysis application 250 includes a record retrieval application 252 that is configured and operable to interpret the unique identifier 16 of each soil sample 12 received and retrieve a respective record 254 associated with the unique identifier 16 from the database 54. Based on the scanned unique identifier 16, the soil analysis application 250 is capable of determining the farm/client name 204 associated with that particular soil sample 12, the field identifier 206 associated with that particular soil sample 12, and the geographic coordinates 210 associated with that particular soil sample 12.

At step 116, the lab performs tests on the soil sample 12 and generates a plurality of test results 258 associated with the soil sample 12. One or more soil testing applications 256 may be associated with the soil laboratory server 50 for generating the test results 258. As illustrated in FIG. 6, in one form the testing application 256 is configured to generate test results 258 that are associated with each respective record 254. As a result, the test results 258 are associated with a particular farm/client name 204, field identifier 206, unique container identifier 16, and geographic coordinates 210. In one form, the test results 258 are stored in database 54 as a function of the unique identifier 16 associated with the soil sample 12, which is represented at step 118.

Figure 7:
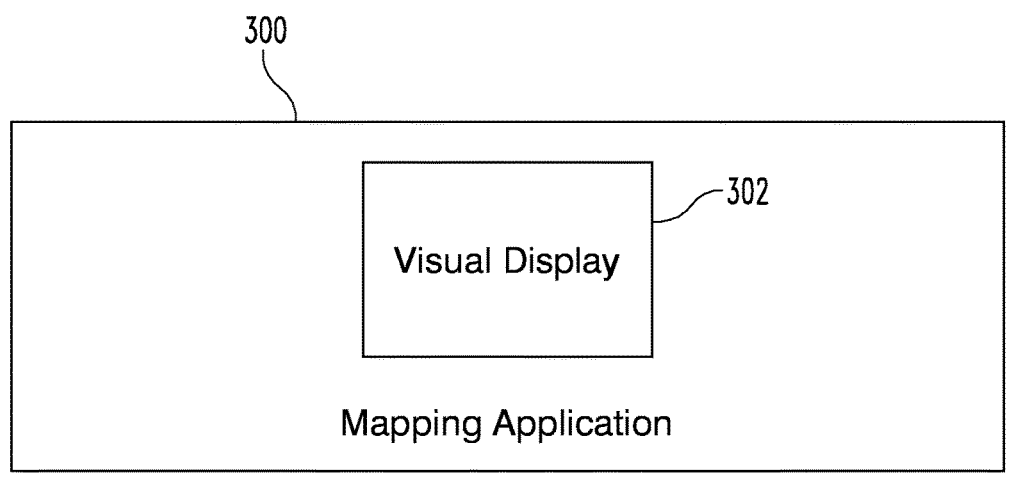
FIG. 7 illustrates a representative mapping application.

In case the soil analysis is done by a third party lab specializing in performing soil tests, the records 254 and test results 258 may then be transmitted to the soil sample server 44 and stored in database 48, which is represented at step 120. At step 121, the test results 258 are automatically linked to the soil sample site or field 10 using the unique container identification 16. Once the test results are received for an entire field 10, one or more test result maps 122 can be generated using a mapping application 300 (see FIG. 7). The mapping application 300 is configured to generate one or more visual displays 302 of the field 10 and place the test results 258 for each specific geographic location of the field 10 on the visual display 302. The visual displays 302 are generated using images of the field 10 obtained from other databases. These images could either be in the form of real photographs or maps. The mapping application 300 uses the geographic coordinates 210 associated with each record 254 to place the test results on the visual displays 302. In one form, the visual displays 302 can be transmitted to the client in the form of an executable file that can be viewed on a computer. In yet another form, the visual displays 302 can be transmitted to the client in the form of a digital file, such as a portable document file (PDF). In other forms, the visual displays 302 can be printed in a traditional paper format and provided to the client.

Figure 8:
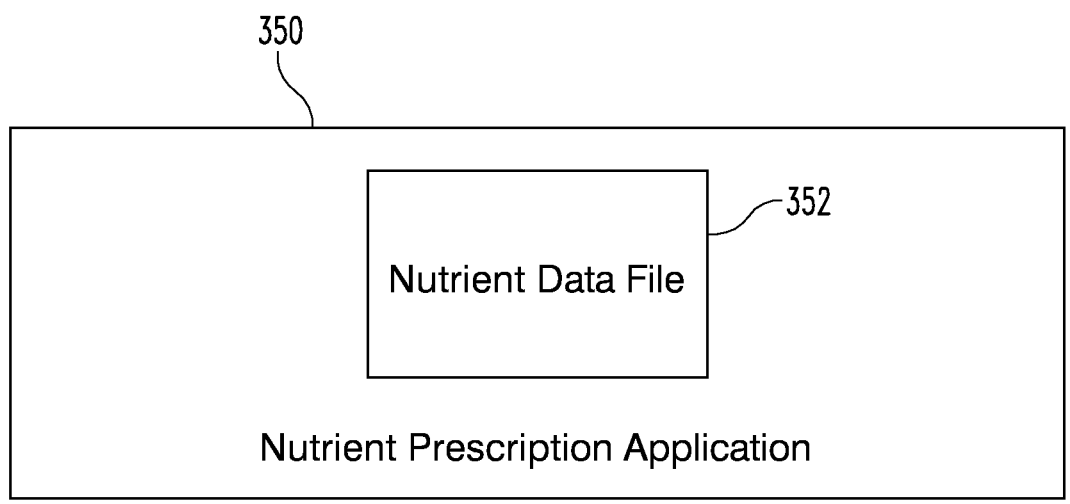
FIG. 8 illustrates a representative nutrient prescription application.

Referring to FIGS. 3, 4, and 8, in yet another form of the present invention the system 20 includes a nutrient prescription application 350. The nutrient prescription application 310 is operable and configured to generate a nutrient data file 312 associated with a respective field 10. The nutrient prescription application 350 generates the nutrient data file 352 as a function of the records 254 and test results 258. The nutrient data file 352 contains data values associated with what level of nutrients need to be added to respective areas of the field 10 based on the test results 258. As such, the level of nutrients (e.g. —fertilizer) applied to one area of the field 10 will be different than in other areas of the field 10. This is because the soil samples 12 were associated with the unique identifier 16, which in turn allowed the soil samples 12 to be associated with respective geographic coordinates 210 of the field 10. Different cells S1-S16 of the field 10 will need different levels of nutrients for a variety of reasons. As such, the nutrient prescription application 350 allows for very specific application of nutrients to different areas of the field 10 instead of a one application fits all type of approach.

In one form, the nutrient data file 352 is transmitted to the fertilizer company server 60, which is represented at step 126 in FIG. 4. In yet another form, the nutrient prescription application 350 is located on the fertilizer company server 60. The nutrient data file 352 is then uploaded to a nutrient applicator 66 that is configured to provide nutrients to the field 10. The nutrient applicator 66 uses the nutrient data file 352 to apply nutrients to the field 10 at the levels they are needed in respective areas of the field 10 as a function of the nutrient data file 352. As such, nutrients are applied at optimum levels in the field 10 by the nutrient applicator 66 thereby avoiding either over or under application of nutrients in specific areas or cells S1-13 of the field 10.

Although various embodiments have been described as having particular features and/or combinations of components, other embodiments are possible having a combination of any features and/or components from any of embodiments as discussed above. As used in this specification, the singular forms "a," "an" and "the" include plural referents unless the context clearly dictates otherwise.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A method, comprising:
    providing access to a plurality of soil sample containers each having a unique identifier associated therewith prior to a user going to a field, wherein each of said soil sample containers are structured to receive at least one soil sample which has been removed from said field with a soil sampling device;
    providing a soil sampling application structured to be displayed on a handheld portable computing device, wherein the handheld portable computing device remains free from interconnection with the soil sampling device as the soil sample is removed from said field;
    providing said unique identifier to said soil sampling application, wherein said unique identifier is associated with one of said plurality of soil sample containers containing said at least one soil sample, and wherein said unique identifier is structured to be input via said handheld portable computing device;
    obtaining a geographic coordinate reading associated with a location in said field from where said soil is removed, wherein said geographic coordinate reading is structured to be providing by said handheld portable computing device; and
    associating said soil sample with said unique identifier and said geographic coordinate reading.

2. The method of claim 1, further comprising storing said unique identifier and said geographic coordinate reading in a database associated with said handheld portable computing device.

3. The method of claim 2, further comprising synching said database associated with, said handheld portable computing device with a server.

4. The method of claim 3, further comprising generating a laboratory work order, wherein the laboratory work order comprises a data file including said unique identifier and said geographic coordinate reading associated with said soil sample.

5. The method of claim 4, further comprising transmitting said data file and said at least one soil sample to a soil laboratory.

6. The method of claim 5, further comprising inputting, said unique identifier on said soil sample container into a laboratory terminal.

7. The method of claim 6, further comprising performing a soil analysis on said at least one soil sample in said soil container and storing lab results from said soil analysis of said soil sample.

8. The method of claim 3, further comprising generating a laboratory work order and providing access to said at least one soil sample to a soil laboratory such that said soil laboratory can perform a soil analysis on said at least one soil sample.

9. The method of claim 8, further comprising generating a test results ma p that is mapped to said field in response to said soil analysis performed by said laboratory.

10. The method of claim 8, further comprising generating a nutrient prescription as a function of said lab results.

11. The method of claim 10, further comprising transmitting said nutrient prescription to an entity for application of nutrients to said field as a function of said nutrient prescription.

12. The method of claim 3, further comprising storing at least one of a farm name and field identifier assigned by a user on the server.

13. The method of claim 1, wherein said unique identifier comprises a barcode, and said providing said unique identifier further comprises scanning said unique identifier with said handheld computing device.

14. The method of claim 1, further comprising generating a grid-like pattern over at least a portion of the field, wherein the grid-like pattern includes a plurality of sample cells.

15. The method of claim 1, wherein the handheld portable computing device comprises a smartphone.

16. A method, comprising:
    providing a soil sample application structured to be displayed on a handheld computing device;
    receiving a unique identifier structured to be input on the handheld computing device, wherein the unique identifier is associated with a soil sample container, and wherein the unique identifier was associated with the soil sample container prior to a user entering a field;
    storing a geographic coordinate reading associated with a location in the field where a user obtained a soil sample, from the field with a soil sampling device, wherein the soil sample container is structured to receive the soil sample, wherein the handheld computing device does not interconnect with the soil sampling device and wherein the application is structured to receive the geographic coordinate reading from the handheld computing device, and wherein; and
    associating the soil sample with the unique identifier and the geographic coordinate reading.

17. The method of claim 16, further comprising storing the unique identifier and the geographic coordinate reading in a database associated with the handheld computing device.

18. The method of claim 17, further comprising syncing said database associated with the handheld computing device with a server.

19. The method of claim 18, further comprising storing a farm name and a field identifier assigned by a user on the server.

20. The method of claim 16, further comprising;
generating a laboratory work order, wherein the laboratory work order includes the unique identifier and said geographic coordinate reading associated with said soil sample; and
transmitting said work order to a soil laboratory.

21. The method of claim 20, further comprising generating a test results map that is mapped to the field in response to the results from a soil analysis performed by the soil laboratory.

22. The method of claim 16, further comprising generating a grid-like pattern over at least a portion of the field, wherein the grid-like pattern includes a plurality of sample cells, and wherein one or more of the soil samples are obtained from one or more of the plurality of sample cells.

23. The method of claim 16, wherein the handheld computing device comprises a smartphone.

24. A system, comprising:
a soil sample application, structured to receive a unique identifier input via a portable handheld computing device, wherein the unique identifier is structured to be input from a soil sample container, wherein the unique identifier is structured to be disposed on the soil sample container prior to going to a field; and
wherein the soil sample application is further structured to obtain a geographic position from the portable handheld computing device at a location where a soil sample is removed from the field with a soil sampling device and disposed in the soil sample container, wherein the soil sample application is further structured to associate the soil sample with the unique identifier and the geographic position, wherein the portable handheld computing device remains free from interconnection with the soil sampling device when the soil sample is removed from the field, and wherein the soil sample application is structured to store the unique identifier and the geographic position in a database.

25. The system of claim 24, wherein the soil sampling application is further structured to sync the database with a server.

26. The system of claim 25, wherein the portable handheld computing device is a smartphone structured to wirelessly sync the database with the server.

27. The system of claim 25, wherein the server is operable to permit a use to generate a laboratory work order.

28. The system of claim 24, wherein the unique identifier comprises a barcode and wherein the portable handheld computing device is structured to scan the barcode.

* * * * *